United States Patent [19]

Shannon et al.

[11] Patent Number: 4,601,858

[45] Date of Patent: Jul. 22, 1986

[54] METHOD FOR PREPARING BISCHLOROFORMATE COMPOSITIONS

[75] Inventors: Thomas G. Shannon, Schenectady; Daniel J. Brunelle, Scotia, both of N.Y.

[73] Assignee: General Electric Company, Schenectady, N.Y.

[21] Appl. No.: 744,348

[22] Filed: Jun. 13, 1985

[51] Int. Cl.$^4$ .................. C07C 69/96; C07C 68/02
[52] U.S. Cl. .................................................. 558/281
[58] Field of Search ........................................ 260/463

[56] References Cited

U.S. PATENT DOCUMENTS 3,189,640  6/1965  Dietrich et al. .................. 260/463
3,254,051  5/1966  Schmitt ............................... 528/199
3,959,335  5/1976  Vernaleken et al. ............... 260/463

*Primary Examiner*—Bernard Helfin
*Attorney, Agent, or Firm*—William H. Pittman; James C. Davis, Jr.; James Magee, Jr.

[57] ABSTRACT

Bischloroformate compositions are prepared by passing gaseous phosgene into an agitated aqueous solution of a di-(alkali metal) salt of an organic dihydroxy compound such as bisphenol A, while maintaining said solution at a temperature within the range of about 0°–50° C. Phosgene passage and agitation are continued until the bischloroformate composition has precipitated. The reaction is typically complete when the pH of the aqueous phase drops below 7.

11 Claims, No Drawings

METHOD FOR PREPARING BISCHLOROFORMATE COMPOSITIONS

This invention relates to the preparation of bischloroformates, and in particular to a relatively simple method for such preparation.

Bischloroformates are known to be useful in the preparation of polycarbonates and similar polymers. In particular, it has been found that bischloroformates can be converted into cyclic polycarbonate oligomers, especially oligomer mixtures. Such oligomer mixtures are a versatile class of compositions showing promise for conversion into polycarbonates under a wide variety of conditions. Reference is made to copending, commonly owned application Ser. No. 704,122, filed Feb. 22, 1985, the disclosure of which is incorporated by reference herein.

A number of methods of making bischloroformates are known in the art. For example, U.S. Pat. No. 3,189,640 describes their preparation by reacting a water-soluble salt off an alkylidene diphenol with phosgene in an aqueous or mixed aqueous-organic system; it also requires the use of a buffer to regulate alkalinity. Other methods, generally employing an organic diluent as well as the aqueous medium, are disclosed in U.S. Pat. Nos. 3,312,661, 3,969,335, 3,966,785 and 3,974,126.

In these methods the bischloroformate dissolves in the organic phase as it is formed, necessitating troublesome separation procedures for isolation. Moreover, a considerable excess of phosgene is usually required. While phosgene is not a particularly expensive chemical reagent, it is highly toxic and care must therefore be taken to avoid its discharge into the atmosphere. Unreacted phosgene is normally destroyed by quenching with sodium hydroxide and neutralizing the sodium carbonate solution thus formed with mineral acid, thus generating a large amount of carbon dioxide. Such protective methods are cumbersome.

A principal object of the present invention, therefore, is to provide an improved method for the preparation of bischloroformate compositions.

A further object is to provide a method which permits the isolation of the bischloroformate in high yield by simple means involving a minimum of processing steps.

A further object is to provide a bischloroformate preparation method which requires a minimum amount of phosgene.

Other objects will in part be obvious and will in part appear hereinafter.

In its broadest sense, the present invention is a method for preparing a composition comprising water-insoluble bischloroformates of organic dihydroxy compounds which comprises passing gaseous phosgene into an agitated solution consisting essentially of water and at least one di-(alkali metal) salt of said organic dihydroxy compound while maintaining said solution at a temperature within the range of about 0°–50° C., and continuing passage of said phosgene and agitation until said bischloroformate composition has precipitated.

The bischloroformate compositions prepared according to the method of this invention generally consist essentially of compounds having the formula

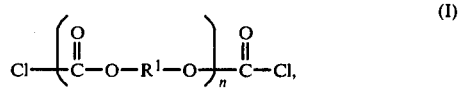

wherein $R^1$ is a divalent aliphatic, alicyclic or aromatic radical and n is at least 1. One of the advantages of the invention is its utility for the preparation of compositions containing a substantial proportion, generally at least about 45% by weight, of the compound wherein n is 1 (hereinafter "monomer bischloroformate") and no more than 10% of compounds wherein n is greater than 3 (hereinafter "higher oligomer bischloroformates"). Substantial proportions of dimer and trimer bischloroformates (wherein n is 2 and 3) are usually also present. The compositions may also contain minor amounts of monochloroformates (especially monomer monochloroformate) and of linear polycarbonate oligomers.

The distributions of the molecular species in the bischloroformate compositions may be determined by reversed phase high pressure liquid-liquid chromatography. The compositions is first reacted with an equimolar mixture of phenol and triethylamine to produce the corresponding phenyl carbonates, which are resistant to hydrolysis under chromatography conditions. The phenyl carbonates are dissolved in a mixture of tetrahydrofuran and water and chromatographed using a relatively non-polar packing, whereupon lower molecular weight constituents are eluted first. For each molecular species, two values are determined and used for identification: the retention time (in minutes) and the area under the ultraviolet absorption peak at 254 nm., which is uniquely identifiable for compounds of this type. Separately prepared linear compounds, including bisphenol A mono- and diphenyl carbonate and the diphenyl carbonate of bisphenol A dimer, may be used as standards for assignment of retention time and 254 nm. absorption. Higher oligomers may be detected by analogy.

The $R^1$ values which are aliphatic or alicyclic in the compounds of formula I generally contain up to about 8 carbon atoms. Suitable $R^1$ values include ethylene, propylene, trimethylene, tetramethylene, hexamethylene, dodecamethylene, 1,4-(2-butenylene), 1,10(2-ethyldecylene), 1,3-cyclopentylene, 1,3-cyclohexylene, 1,4-cyclohexylene, m-phenylene, p-phenylene, 4,4'-diphenylene, 2,2-bis(4-hydroxyphenylene)propylidene, benzene-1,4-dimethylene (which is a vinylog of the ethylene radical and has similar properties) and similar radicals such as those which correspond to the dihydroxy compounds disclosed by name or formula (generic or specific) in U.S. Pat. No. 4,217,438, the disclosure of which is incorporated by reference therein. The $R^1$ values are usually aromatic and preferably have the formula

wherein each of $A^1$ and $A^2$ is a single-ring divalent aromatic radical and Y is a bridging radical in which one or two atoms separate $A^1$ from $A^2$. The free valence bonds in formula II are usually in the meta or para positions of $A^1$ and $A^2$ in relation to Y.

In formula II, the $A^1$ and $A^2$ values may be unsubstituted phenylene or substituted derivatives thereof, illustrative substituents (one or more) being alkyl, alkenyl (e.g., crosslinkable-graftable moieties such as vinyl and allyl), halo (especially chloro and/or bromo), nitro, alkoxy and the like. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ and $A^2$. It is most often a hydrocarbon radical and particularly a saturated radical such as methylene, cyclohexylmethylene, 2-[2.2.1]-bicycloheptylmethylene, ethylene, isopropylidene neopentylidene, cyclohexylidene, cyclopentadecylidene, cyclododecylidene or adamantylidene, gem-alkylene radical. Also included, however, are unsaturated radicals and radicals which are entirely or partially composed of atoms other than carbon and hydrogen, such as 2,2-dichloroethylidene. For reasons of availability and particular suitability for the purposes of this invention, the preferred radical of formula II is the 2,2-bis(4-phenylene)propylidene radical, which is derived from bisphenol A and in which Y is isopropylidene and $A^1$ and $A^2$ are each p-phenylene.

The method of this invention utilizes an aqueous solution consisting essentially of at least one di-(alkali metal) salt of an organic dihydroxy compound, said dihydroxy compound generally having the formula $R^1(OH)_2$, wherein $R^1$ is as previously defined. The alkali metal in said salt is generally lithium, sodium or potassium, preferably sodium or potassium and most preferably sodium. The concentration of the dihydroxy compound salt solution is not critical so long as said solution is homogeneous. Said concentration is most often about 0.2–1.0 M and preferably about 0.4–0.75 M.

An important feature of the invention is the fact that the solution consists essentially of water and said di-(alkali metal) salt. That is, those ingredients are the only ones which contribute to the essential characteristics and advantages of the invention. The invention is noteworthy in that it does not require the presence of materials such as buffers and organic solvents. It is, however, within the scope of the invention to ensure complete conversion of the dihydroxy compound to its di-(alkali metal) salt by employing an excess of alkali metal base, typically alkali metal hydroxide, in the solution. The amount of excess employed is generally up to about 50%, with about 25–40% being preferred.

According to the invention, phosgene is passed into the solution while it is agitated by conventional means such as stirring or shaking. Thorough agitation is preferred in order to minimize agglomeration of product. The temperature of the reaction mixture during phosgene addition is an important part of the invention. If it is too low, the reaction proceeds too slowly to be conveniently practicable; if it is too high, hydrolysis of the bischloroformates may occur with the formation of monochloroformates and/or oligomeric dihydroxy compounds. The temperature should be maintained in the range of about 0°–50° C. and preferably about 0°–30° C. Since the reaction is quite exothermic, conventional cooling means may be necessary if the process is practiced on a large scale.

While the rate of addition of phosgene is not a critical aspect of the invention, it is generally found that high addition rates promote rapid reaction with a decrease in the basicity of the solution, thus suppressing hydrolysis of the bischloroformates. In general, it is preferred to coordinate conditions such as phosgene addition rate and degree of cooling of the reaction mixture so as to permit phosgene addition to be completed in about 20 minutes or less. Under most circumstances, there is no particular advantage in an addition period of less than 5 minutes.

During the process, the desired bischloroformate composition precipitates from the solution. It is frequently advantageous to remove it as rapidly as possible from the reaction mixture in order to prevent hydrolysis. Removal may be effected by conventional means such as continuous cycling through a filter.

The degree of completion of the reaction may be determined by measuring the pH of the aqueous phase. Since phosgene is consumed by reaction both with the di-(alkali metal) salt and with any base present in excess, the reaction is complete when the pH of the aqueous phase drops below 7 (i.e., when the solution becomes acidic). It is generally found that this occurs when an approximately stoichiometric amount of phosgene has been introduced.

Following preparation of the chloroformate composition by the method of this invention, individual components of the composition, such as monomer bischloroformate, may be separated by conventional means such as distillation, chromatography, fractional crystallization or the like. Such operations are frequently unnecessary, however, since for many purposes the bischloroformate composition may be used without purification.

As previously mentioned, the method of this invention is using for preparing bischloroformate compositions containing a substantial proportion, generally at least about 45% by weight, of monomer bischloroformate. This feature of the invention is particularly unexpected in view of the disclosure of U.S. Pat. No. 3,254,051. According to that patent, monochloroformates are prepared by phosgenating an aqueous solution or suspension containing substantially equimolar proportions of an alkali metal or alkaline earth metal hydroxide and an aromatic dihydroxy compound. That is, an aqueous system containing the mono-(alkali metal) salt of the dihydroxy compound is phosgenated. According to Example A of that patent, the monochloroformate precipitates and can be recovered by filtration.

In the present invention, the di-(alkali metal) salt is employed rather than the mono-(alkali metal) salt. As a logical extension of the teachings of U.S. Pat. No. 3,254,051, it might be expected that an intermediate product formed in the present method would be the monomer monochloroformate mono-(alkali metal) salt. This could be followed by various condensations between chloroformate and alkali metal salt moieties in monomer di-(alkali metal) salt, bischloroformate and monochloroformate mono-(alkali metal) salt, thereby producing large quantities of oligomer bischloroformates with the consumption of substantially all monomer bischloroformate. The fact that the product which precipitates contains large amounts of monomer bischloroformate is therefore quite unexpected. It is also advantageous, since bischloroformate compositions containing substantial proportions of monomer bischloroformate and relatively small proportions of higher oligomer bischloroformates are particularly valuable for the preparation of the aforementioned cyclic polycarbonate oligomers.

The method of this invention is illustrated by a series of examples in which aqueous solutions of bisphenol A disodium salt were prepared by adding bisphenol A to aqueous sodium hydroxide solutions with stirring and gentle heating until complete dissolution took place.

The solutions were then cooled to 30° C. and stirred rapidly at that temperature as phosgene was bubbled through until the pH fell below 7, with an approximately stoichiometric amount of phosgene being consumed in each instance. The bischloroformate composition precipitated as a finely divided white solid during phosgene addition. It was removed by filtration and washed with aqueous hydrochloric acid and water. A sample of the composition was reacted with phenol and triethylamine and analyzed as described hereinabove.

The results are given in the following table. The column labeled "Polycarbonate" refers to the linear polycarbonate oligomers identified hereinabove.

$$-A^1-Y-A^2- \qquad (II)$$

wherein each of $A^1$ and $A^2$ is a single-ring divalent aromatic radical and Y is a bridging radical in which 1 or 2 atoms separate $A^1$ from $A^2$.

4. A method according to claim 3 wherein the temperature is in the range of about 0°–30° C.

5. A method according to claim 4 wherein the concentration of di-(alkali metal) salt in the solution is about 0.2–1.0 M.

6. A method according to claim 5 wherein the reaction is continued until the pH of the aqueous phase drops below 7.

|     |                       |                            |              |                              |                        |                   | Product distribution, %          |                                   |                            |                             |                                             |                       |
|-----|-----------------------|----------------------------|--------------|------------------------------|------------------------|-------------------|----------------------------------|-----------------------------------|----------------------------|-----------------------------|---------------------------------------------|-----------------------|
| Ex. | Mmol. bisphenol A     | Bisphenol A conc., M       | Mmol. NaOH   | Phosgene Rate, g./min.       | addn. Time, min.       | Temp., deg. C.    | Monomer bischloroformate         | Monomer monochloroformate         | Dimer bischloroformate     | Trimer bischloroformate     | Higher oligomer bischloroformates           | Polycarbonate         |
| 1   | 50                    | 0.33                       | 100          | 1.0                          | 9.9                    | 35                | 51                               | 6                                 | 11                         | 8                           | 7                                           | 5                     |
| 2   | 50                    | 0.50                       | 100          | 1.0                          | 9.9                    | 40                | 48                               | 9                                 | 12                         | 10                          | 10                                          | 1                     |
| 3   | 100                   | 1.0                        | 200          | 2.0                          | 9.9                    | 30                | 70                               | 10                                | 4                          | 2                           | 1                                           | 4                     |
| 4   | 100                   | 1.0                        | 240          | 2.0                          | 9.9                    | 20                | 60                               | 8                                 | 13                         | 8                           | 5                                           | 1                     |
| 5   | 100                   | 0.67                       | 220          | 4.2                          | 4.7                    | 35                | 49                               | 15                                | 13                         | 8                           | 4                                           | 3                     |
| 6   | 100                   | 0.67                       | 220          | 2.0                          | 9.9                    | 30                | 51                               | 13                                | 13                         | 7                           | 5                                           | 5                     |
| 7   | 100                   | 0.67                       | 240          | 2.0                          | 9.9                    | 30                | 55                               | 9                                 | 12                         | 8                           | 5                                           | 2                     |
| 8   | 100                   | 0.67                       | 240          | 1.0                          | 19.8                   | 30                | 45                               | 14                                | 14                         | 7                           | 4                                           | 7                     |
| 9   | 100                   | 0.67                       | 280          | 2.0                          | 9.9                    | 30                | 70                               | 4                                 | 12                         | 7                           | 6                                           | 0                     |
| 10  | 100                   | 0.67                       | 220          | 2.0                          | 9.9                    | 15                | 50                               | 8                                 | 16                         | 9                           | 6                                           | 4                     |
| 11  | 100                   | 0.67                       | 220          | 2.0                          | 9.9                    | 5                 | 55                               | 9                                 | 10                         | 6                           | 4                                           | 0                     |
| 12  | 100                   | 0.67                       | 220          | 2.0                          | 9.9                    | 50                | 47                               | 17                                | 16                         | 9                           | 6                                           | 9                     |
| 13  | 100                   | 0.67                       | 300          | 2.0                          | 9.9                    | 50                | 69                               | 5                                 | 11                         | 7                           | 7                                           | 0                     |
| 14  | 300                   | 0.67                       | 840          | 4.0                          | 14.9                   | 50                | 49                               | 14                                | 13                         | 9                           | 5                                           | 1                     |

What is claimed is:

1. A method for preparing a composition comprising water-insoluble bischloroformates of organic dihydroxy compounds which comprises passing gaseous phosgene into an agitated solution consisting essentially of water and at least one di-(alkali metal) salt of said organic dihydroxy compound while maintaining said solution at a temperature within the range of about 0°–50° C., and continuing passage of said phosgene and agitation until said bischloroformate composition has precipitated.

2. A method according to claim 1 wherein the dihydroxy compound has the formula $R^1(OH)_2$, wherein $R^1$ is a divalent aliphatic, alicyclic or aromatic radical.

3. A method according to claim 2 wherein $R^1$ has the formula

7. A method according to claim 6 wherein the conditions are coordinated so as to permit phosgene addition to be completed in about 20 minutes or less.

8. A method according to claim 3 wherein $A^1$ and $A^2$ are p-phenylene and Y is isopropylidene.

9. A method according to claim 8 wherein the concentration of di-(alkali metal) salt in the solution is about 0.2–1.0 M.

10. A method according to claim 9 wherein the reaction is continued until the pH of the aqueous phase drops below 7.

11. A method according to claim 10 wherein the conditions are coordinated so as to permit phosgene addition to be completed in about 20 minutes or less.

* * * * *